(12) United States Patent
Bandyopadhyay et al.

(10) Patent No.: US 10,900,909 B2
(45) Date of Patent: Jan. 26, 2021

(54) TRANSMITTANCE BASED SYSTEM/KIT FOR POINT-OF-CARE QUANTIFICATION OF BIOMARKERS SAMPLE AND USE THEREOF

(71) Applicant: INDIAN INSTITUTE OF TECHNOLOGY, GUWAHATI, Guwahati (IN)

(72) Inventors: Dipankar Bandyopadhyay, Guwahati (IN); Nilanjan Mandal, Guwahati (IN); Satarupa Dutta, Guwahati (IN)

(73) Assignee: INDIAN INSTITUTE OF TECHNOLOGY, GUWAHATI, Guwahati (IN)

( * ) Notice: Subject to any disclaimer, the term of this patent is extended or adjusted under 35 U.S.C. 154(b) by 329 days.

(21) Appl. No.: 15/773,456

(22) PCT Filed: Jan. 16, 2017

(86) PCT No.: PCT/IN2017/050023
§ 371 (c)(1),
(2) Date: May 3, 2018

(87) PCT Pub. No.: WO2017/208249
PCT Pub. Date: Dec. 7, 2017

(65) Prior Publication Data
US 2018/0321158 A1    Nov. 8, 2018

(30) Foreign Application Priority Data

May 31, 2016   (IN) .............................. 201631018620

(51) Int. Cl.
*G01N 21/78*     (2006.01)
*G01N 21/77*     (2006.01)
(Continued)

(52) U.S. Cl.
CPC ....... *G01N 21/78* (2013.01); *A61B 5/150022* (2013.01); *A61B 5/150358* (2013.01);
(Continued)

(58) Field of Classification Search
CPC ................... G01N 21/78; G01N 21/77; G01N 2021/7783; A61B 5/150022;
(Continued)

(56) References Cited

U.S. PATENT DOCUMENTS

| 3,557,018 A | 1/1971 | Scheuerbrandt |
| 3,888,739 A | 6/1975 | Whetzel et al. |

(Continued)

FOREIGN PATENT DOCUMENTS

| CN | 102288559 A | 12/2011 |
| EP | 0141298 A1 | 5/1985 |

(Continued)

OTHER PUBLICATIONS

International Search Report for PCT/IN2017/050023.

*Primary Examiner* — Jennifer Wecker
*Assistant Examiner* — Michael Paul Shimek
(74) *Attorney, Agent, or Firm* — The PL Law Group, PLLC

(57) ABSTRACT

A transmittance based system/kit for point-of-care quantification of biomarker samples includes a stage supporting a detection unit, an optical transmittance unit and a signal processing unit. The detection unit comprising reactive substrate is capable of undergoing a specific biomarker sample interactive reaction and generating a quantifiable optical signal proportional to the concentration of the said biomarker sample wherein the intensity of the color varies with the concentration of the analyte in the bio-sample. The optical transmittance unit, comprises a sample stage integrated with the light source and a photodetector, converting (Continued)

quantifiable optical signal transmitted through the reagent coated substrate detection unit to electrical signals, a signal processing unit connected to the said optical transmittance unit transduces the analogue electrical signal into the digital display signal. The simple, single step, cost-effective easily disposable system/kit is useful for point-of-care detection of important biomarkers such as amylase, creatinine, albumin, among others.

13 Claims, 5 Drawing Sheets

(51) Int. Cl.
  *C12Q 1/40* (2006.01)
  *A61B 5/1455* (2006.01)
  *A61B 5/15* (2006.01)
  *A61B 5/145* (2006.01)

(52) U.S. Cl.
  CPC ........ *C12Q 1/40* (2013.01); *C12Y 302/01001* (2013.01); *G01N 21/77* (2013.01); *A61B 5/1455* (2013.01); *A61B 5/14546* (2013.01); *G01N 2021/7783* (2013.01)

(58) Field of Classification Search
  CPC .......... A61B 5/150358; A61B 5/14546; A61B 5/1455; C12Q 1/40; C12Y 302/01001
  See application file for complete search history.

(56) References Cited

U.S. PATENT DOCUMENTS

| | | |
|---|---|---|
| 4,000,042 A | 12/1976 | Adams |
| 4,172,765 A | 10/1979 | Keyes |
| 4,233,403 A | 11/1980 | Menson et al. |
| 4,963,479 A | 10/1990 | Chavez et al. |
| 5,043,436 A | 8/1991 | Ogawa |
| 5,180,663 A | 1/1993 | Bruns et al. |
| 5,264,345 A | 11/1993 | Schmidt et al. |
| 5,319,078 A | 6/1994 | Ikenaka |
| 5,607,838 A | 3/1997 | Hattori et al. |
| 2007/0013908 A1 | 1/2007 | Lee et al. |
| 2010/0136521 A1 | 6/2010 | Yoon |
| 2013/0092846 A1 | 4/2013 | Henning et al. |
| 2014/0001058 A1* | 1/2014 | Ghaffari .................. G01N 27/02 205/792 |

FOREIGN PATENT DOCUMENTS

| | | |
|---|---|---|
| WO | WO 01/081617 A1 | 11/2001 |
| WO | WO2013/125386 A1 | 8/2013 |
| WO | WO 2013125386 A1 * | 8/2013 |
| WO | WO2015143387 A1 | 9/2015 |

* cited by examiner

Isometric View
Scale: 1:1

Right view

Front view

Left view

Top view

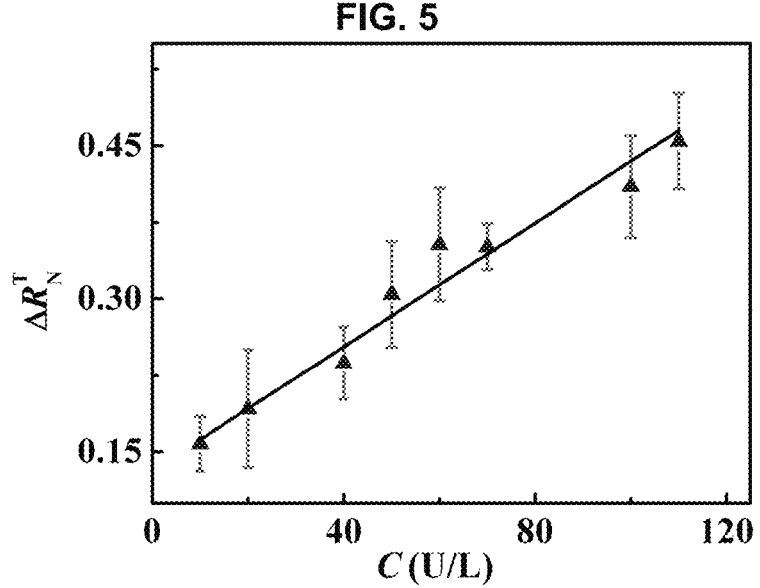

TRANSMITTANCE BASED SYSTEM/KIT FOR POINT-OF-CARE QUANTIFICATION OF BIOMARKERS SAMPLE AND USE THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/IN2017/050023, filed Jan. 16, 2017, which claims priority to the benefit of India Patent Application No. 201631018620 filed in the India Intellectual Property Office on May 31, 2016, the entire contents of which are incorporated herein by reference.

FIELD OF THE INVENTION

The present invention provides a system/kit for quantitative detection of biomarkers. More specifically, the present invention provides a transmittance based system/kit for point-of-care testing and quantitative detection of clinically important biomarker samples. The said system/kit comprises detection unit comprising a reactive substrate capable of undergoing a specific biomarker sample interactive reaction, generates a quantifiable optical signal proportional to the concentration of the said biomarker sample by employing transmittance based optoelectrochemical technique to measure the variations in the color intensities of the pre reagent treated substrates thereby estimating the concentrations of the biomarkers in the biological samples with subsequent digital display of the same. Advantageously, the system/kit of the present invention enables conversion of a chemical response into an optical signal, which is then converted to an analogue electrical and subsequently to a digital signal through one step process for user friendly and faster point-of-care testing and quantitative detection of clinically important biomarker samples.

BACKGROUND ART

The assessment of health conditions generally involves qualitative and quantitative estimation of enzymes, hormones, vitamins, minerals, bacteria, virus, and other biomarkers. Conventional diagnostic methodologies involve pathological tests using sophisticated tools, which are generally carried out in centralized agencies by medical experts. However, in developing countries with limited resource and infra-structure such sophisticated diagnostic technologies are not affordable to a greater section of population. In this direction, in the recent times, the point-of-care testing (POCT) or bedside testing devices have been emerging as a suitable alternative for the conventional diagnostic methods to provide diagnosis at the site of the patient. Most of the commercially available POCT devices are portable and handheld, user friendly, affordable, rapid, and robust, which also make them potential candidates for clinical diagnosis (Chin et al., 2011; Nat. Med. 17, 1015-1019; Li et al. 2014, Electrophoresis. 35, 1152-1159). These devices are also expected to help the patients to understand the extent of an ailment and also to decide on their visit to the medical experts. For example, the commercially available instant glucose meter, blood pressure meters, or the pregnancy or urine test kits are some very successful point-of-care tools at our disposal. However, the presently available POCT tools are rather limited and there are many of the other essential biomarkers, which require frequent monitoring to ensure a minimum quality of life for the human beings.

In this direction, one of the very important biomarker that has no POCT device is $\alpha$-amylase enzyme (endo-1,4-$\alpha$-d-glucan glucanohydrolase, EC 3.2.1.1), which is estimated to detect a host of diseases while the blood culture is performed (Zajoncová et al., 2004, Biosens. Bioelectron. 20, 240-245). In general, amylase is produced in human pancreas and salivary glands for the purpose of hydrolyzing starch into simple sugars (Metzler, 2003 Biochemistry: The Chemical Reactions of Living Cells. Elsevier Science, pp. 161-175). The elevated or diminished levels of it in the blood, saliva, or urine indicate health disorder (Wilkins, 2009, Diagnostic Tests Made Incredibly Easy! Lippincott Williams & Wilkins, pp. 68). Its increased level is associated with acute pancreatitis, pancreatic cancer, salivary gland infection, bile duct blockage, gastroenteritis etc., whereas pancreatic damage, kidney disease, toxaemia of pregnancy can decrease the level of amylase in the body fluids. Over the years, many different techniques for amylase measurement have been invented. Assays to estimate $\alpha$-amylase activity can be broadly divided into three main types: (1) measurement of by-products formed as a result of starch hydrolysis (Zajoncová et al., 2004 Biosens. Bioelectron. 20, 240-245; Yamaguchi et al., 2005, Biomedical Microdevices. 7, 295-300). (2) colorimetric or flourometric methods (Murayama et al., 2006 Bioorganic & Medicinal Chemistry 14, 3691-3696; Attia et al., 2014, Analyst. 139, 793-800) and (3) measurement of consumption of natural substrates of $\alpha$-amylase directly or indirectly (Wu et al., 2007, Sens. Actuators, B. 121, 476-481; Sasaki et al., 2008, J. Agric. Food Chem. 56, 1091-1096).

In particular, spectrophotometric techniques based on absorbance studies of amylase sensitive substrates are by far among the most widely employed methods for estimation of the activity of $\alpha$-amylase which is disclosed in various prior patents [U.S. Pat. No. 4,963,479 (1990); U.S. Pat. No. 3,888,739(1975); U.S. Pat. No. 4,000,042(1976); U.S. Pat. No. 4,233,403(1980); U.S. Pat. No. 5,043,436(1991); U.S. Pat. No. 5,264,345(1993); U.S. Pat. No. 5,319,078(1994); U.S. Pat. No. 5,607,838(1997)]. Though the method is perhaps the most accurate and reliable, this methodology is costly, requires experts for analysis, and is not readily accessible to common people. Further, the sensitivity to turbidity and coloration of the test solution are the major two technological shortcomings of the spectrophotometric methods (Sakačet al., 2011, Talanta. 83, 1606-1612).

Another common method for amylase measurement is electrochemical method employing complex flow injection type systems (Zajoncová et al., 2004 Biosens. Bioelectron. 20, 240-245; Yamaguchi et al., 2005, Biomedical Microdevices. 7, 295-300; Mahosenaho et al., Microchim. Acta. 170, 243-249.; Sakač et al., 2011 Talanta. 83, 1606-1612); U.S. Pat. No. 4,172,765(1979); U.S. Pat. No. 45,472,809 (1985)). Other methods used for the determination of $\alpha$-amylase include colorimetry (CN102288559A), fluorometry (Zhang et al., 1990 Anal. Chim. Acta. 236, 251-256; Murayama et al., 2006), isoelectric focusing (Takeuchi et al., 1975 Clin. Chim. Acta. 60, 207-213), electro kinetic processes (Watanabe et al., 1998, Electrophoresis. 19, 2331-2337), chromatography (Battershell and Henry, 1990, J. Cereal Sci. 12, 73-81), weight based detections (Sasaki et al., 2008, J. Agric. Food Chem. 56, 1091-1096), electromagnetic sensing (Wu et al., 2007, Sens. Actuators, B. 121, 476-481) and immunological methods (Svens et al., 1989. Clin. Chem. 35, 662-664, U.S. Pat. No. 5,180,663(1993)).

The major limitation associated with the aforementioned methodologies is that none of them show promise to evolve into a POCT device following the WHO guideline to be ASSURED—affordable, sensitive, specific, user-friendly, rapid and robust, equipment free, and deliverable.

Use of open source electronic module is known in the area of POCT healthcare devices (Boppart and Richards-Kortum, 2014, Sci. Transl. Med. 6(253), 1-25; Van Schepdael, 2016, Chromatography. 3, 1-12). Previously, researchers have extensively used the open source module for the development of POCT device for the detection of optical (US 20070013908A1; US 20100136521A1; US20130092846A1; Anzalone et al., 2013, Sensors. 13, 5338-5346; Verbarg et al., 2013, Anal. Chem., 85, 4944-4950; Kelley et al., 2014, Sensors. 14, 7142-7155.; Li et al., 2014, Analyst. 139, 823-830; Bosse et al., 2015, PLOS ONE. 10(11), 1-21.), electrochemical (Kaushik et al., 2015, Int. J. Nanomed. 10, 677-685), electromagnetic (Verbarg et al., 2013; Anal. Chem., 85, 4944-4950; Mitchell et al., 2014, Biosens. Bioelectron. 54, 229-236), electrophoretic (Drevinskas et al., 2014, Electrophoresis. 35, 2401-2407), and immunological signals (Verbarg et al., 2013; WO2015143387 A1, 2015).

Dutta et al., 2016, Biosens. Bioelectron. 78, 447-453 disclosed a principle involving multiple steps for detecting the change in color on a paper surface, suitable for point-of-care quantification of biomarker, wherein the optical signal generated from the chemical response is rudimentarily converted into an analogue electrical signal using a commercially available photoresistor integrated with a commercially available digital multimeter. While this publication reported for the first time a principle involving multiple steps for detection of the variation of electrical signal with concentration of the biomarker and constituted an advancement in the related art, there has been a continuing need in the art to further simplify the methodology and develop improved systems/kits such as to enable a one step, ready, and faster quantification of biomarkers and which can be readily applicable for different bio markers to serve wider end uses and applications thereof in the related art.

SUMMARY

It is thus the basic object of the present invention to provide for a simple and compact transmittance based system/kit for point-of-care detection of clinically important biomarker samples and quantitative measurement of the biomarkers.

In another object, the present invention provides a transmittance based system/kit for point-of-care detection of biomarkers comprising processing unit with display for ready displaying of the quantified level of the biomarker.

Another object of the present invention is to provide a transmittance based POCT system/kit which would be sensitive to very low concentration of analytes.

In a still further object, the said transmittance based POCT system/kit adapted for automatic conversion of the optical signal generated from the chemical reaction to electrical and subsequently to the digital display signal in one step for ready and faster quantification of biomarkers and the like.

A still further object of the invention is to provide for a transmittance based POCT system/kit, which avoids the need of experts for handling and operation.

Another object of the present invention is to provide for an easily disposable, biocompatible, biodegradable reactive substrate detection unit for colorimetric assays.

Yet another object of the present invention provides for a transmittance based POCT system/kit which is energy efficient, cost-effective, portable, and fast.

Thus, according to the basic aspect of the present invention there is provided a transmittance based system/kit for point-of-care quantification of biomarker samples comprising:

a stage for supporting a detection unit comprising reactive substrate capable of undergoing a specific biomarker sample interactive reaction and generating a quantifiable optical signal proportional to the concentration of the said biomarker sample;

an optical transmittance unit;

a signal processing unit operatively connected to said optical transmittance unit for quantification of said biomarker sample based on the optical signal generated from the substrate-biomarker sample reaction.

Another aspect of the present invention provides a transmittance based system/kit wherein said signal processing unit comprises a display unit for ready displaying of the quantified level of the biomarker.

In another aspect, the present invention provides a transmittance based system/kit wherein said reactive substrate is selected from paper based reactive substrates including substrates selected from paper coated with starch-iodine for amylase detection, paper coated with picric acid and sodium hydroxide for creatinine detection, and paper coated with bromophenol blue for albumin detection.

Yet another aspect of present invention relates to a transmittance based system/kit wherein said reactive substrate comprises pre reagent-treated substrate based on the selective biomarker sample to be quantified and can include combinations selected from:

for α-amylase enzyme biomarker sample providing starch-iodine reagent treated paper substrate;

for creatinine biomarker sample providing picric acid and sodium hydroxide reagent treated paper substrate;

for albumin biomarker sample providing bromophenol blue reagent treated paper substrate.

A further aspect of the present invention provides a transmittance based system/kit wherein the said optical transmittance unit comprises a light source and a photodetector, which confines the sample stage from two sides, wherein the light source illuminates the reagent coated paper detection unit and the transmitted light through the paper is collected on a photodetector;

said photodetector transducing said quantifiable optical signal transmitted through the reagent coated paper detection unit to electrical signal; and said signal processing unit transducing analogue electrical signal produced in the transmittance unit into a digital display signal.

According to another aspect of the present invention there is provided a transmittance based system/kit wherein said optical transmittance unit comprise said detection unit integrated with light emitting source preferably LED and a photo detector preferably LDR operatively connected to said signal processing unit including a microprocessor with said detection unit comprising a substrate chamber with dark/black surroundings to facilitate signal processing as a single step process.

According to another aspect of the present invention there is provided a transmittance based system/kit wherein analogue electrical signal obtained from LDR is automatically converted into a digital signal through said signal processing unit for digital display, said signal processing unit calibrated to measure the biomarker level.

Another aspect of the present invention relates to a transmittance based system/kit wherein said substrate comprises filter paper cut into pieces of appropriate size and shape and pretreated with said reagent and dried.

In another aspect, the present invention relates to a transmittance based system/kit wherein the reactive substrate having the said reagent is colored, which upon reaction with said biomarker sample generates said quantifiable optical signal proportional to the concentration of the said biomarker sample.

In a further aspect, the present invention relates to a transmittance based system/kit wherein the sample stage is made of black polymer sheets and glass slides; said light source is a commercially available light emitting diode (LED); and said photodetector is a commercially available light dependent resistor (LDR).

Yet another aspect of the present invention relates to a transmittance based system/kit wherein said optical transmittance unit comprises of a sample stage confined between an illumination source as LED and a photodetector as LDR in such a manner that light from the light source falls on the photodetector after transmitted through the paper detection units.

Another aspect of the present invention relates to a system/kit wherein the signal processing unit includes calibration of variation of known amylase concentration with the variation in the coloration stabilized on the substrate.

Yet another aspect of the present invention relates to a method for point-of-care quantification of biomarkers sample involving the system/kit comprising: providing on said stage reactive substrate capable of undergoing a specific biomarker sample interactive reaction;

reacting the said reactive substrate with a biomarker sample for quantification and generating a quantifiable optical signal proportional to the concentration of the said biomarker sample; and carrying out signal processing for quantification of said biomarker sample based on the optical signal generated from the substrate-biomarker sample reaction.

A further aspect of present invention relates to a method comprising selectively providing the color of the paper substrate having pretreated reagent, which upon interaction with biomarker sample leads to a very specific reaction leading to the fading of the color of the reagent coated paper;

wherein the intensity of the color varies with the concentration of the analyte in the bio-sample.

In a still further aspect, the present invention provides a method comprising (a) providing color of the reagent coated paper substrate as Prussian blue colored starch-iodine coated paper, which upon interaction with aqueous α-amylase solution on the blue colored starch-iodine coated paper detection units leads to a very specific reaction leading to the fading of the Prussian blue color of the paper; and (b) wherein the intensity of the Prussian blue color varies with the concentration of the amylase in the bio-sample;

(c) wherein the reduction in the intensity of the blue coloration on the paper detection units can be observed with increase in the amylase in the aqueous solution.

In yet another aspect, the present invention provides a method wherein (a) the intensity of the transmitted light coming out of the paper detection unit varied with the fading of the blue coloration on the paper surface with increase in the amylase activity;

(b) the variations in the intensity of the transmitted light with the variation in amylase activity generated different analogue electrical signals on the LDR;

(c) the transmittance based optical signal originating from the chemical response of the reagent coated paper substrate is converted into an analogue electrical signal by the calibrated signal processing unit; and (d) displayed in the display means or report generated based thereon with the help of the calibrated signal processing unit.

BRIEF DESCRIPTION OF THE DRAWINGS

The details of the invention, its objects, and advantages are explained hereunder in greater detail in relation to the following non-limiting accompanying figures and examples.

FIG. 5 illustrates the experimental calibration curve showing the variation of the normalized resistance difference ($\Delta R_N^T$) with concentration of α-amylase (C).

DETAILED DESCRIPTION

Figure 1A:
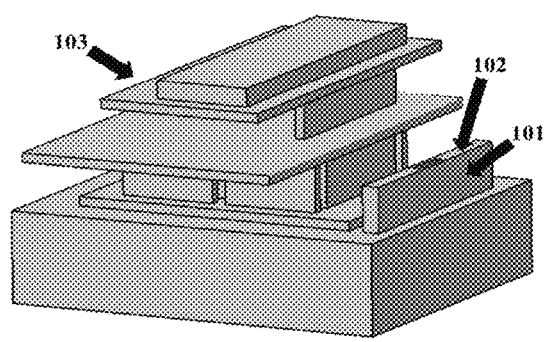
FIG. 1A represents the schematic diagram of the optoelectronic device of the present invention with tentative locations of the different elements.
Figure 1B:
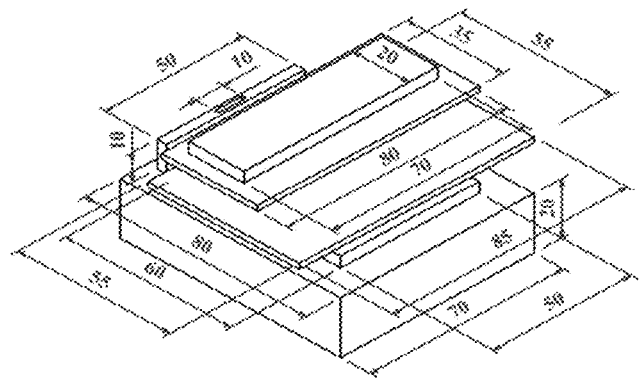
FIGS. 1B to 1F represent the isometric, right, front, left, and top views with the dimensions of the said device, respectively.
Figure 1C:
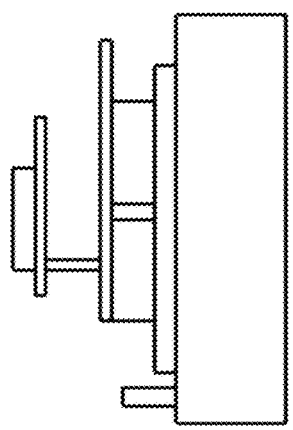
Figure 1D:
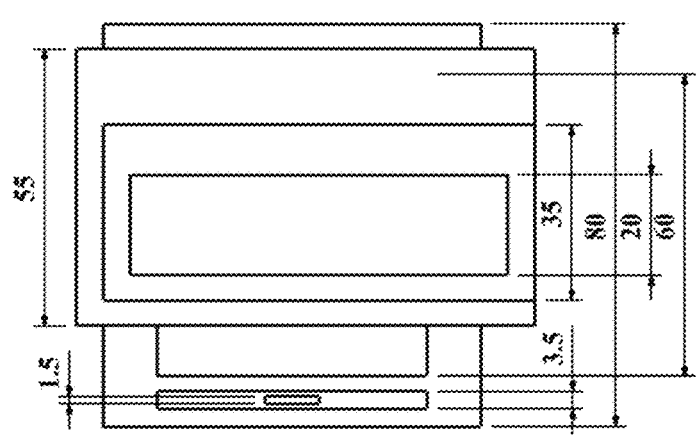
Figure 1E:
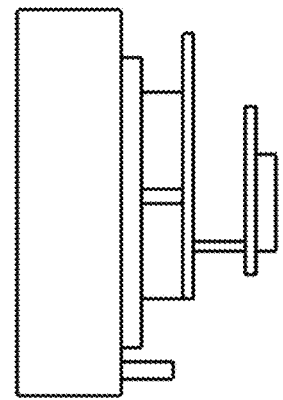
Figure 1F:
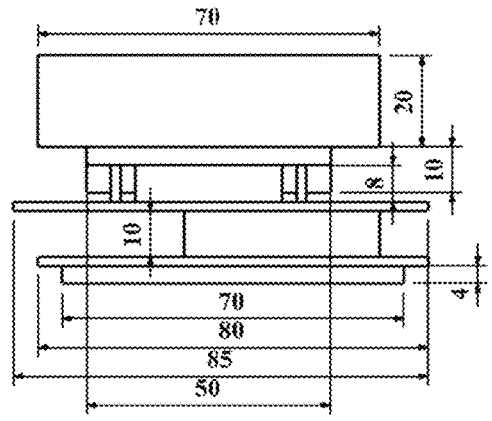

As discussed herein before the present invention provides for a novel transmittance based system/kit for point-of-care quantification of biomarker samples. The said system/kit measures the color variations on a pre reagent treated reactive substrate detection unit thereby detecting the levels of biomarkers in different bioanalytes. Most of the previously reported technologies are reflectance based whereas the present invention is based on optoelectrochemical technology, which can measure the variation in the color on a reactive substrate detection unit and immediately converts it into an electrical signal and subsequently into a digital display signal through a signal processing unit.

In accordance with a preferred aspect of the present invention, the system of the present advancement provides an integrated system for quantification of the biomarker sample involving conversion of optical signal to electrical and digital display signals in one step process.

In the system/kit of the present invention the photoresistor, reactive substrate, and the LED are integrated strategically with a microcontroller unit. The assembly is adapted to be selectively calibrated by the specific biomarker in the beginning to be ready to detect the unknown amount of the biomarker sample in the blood serum. Such integrated system/kit constitutes advancement for ready and faster quantification of biomarkers and the like.

The reaction between the biomarker poured from a liquid sample on the reactive substrate detection unit pre-coated with a colored reagent specific to the biomarker leads to a variation in the colorimetric signal, which is in commensuration to the concentration of the biomarker in the liquid sample. The variation in the colorimetric signal is quantified by the transmittance based optoelectrochemical system/kit comprising a sample stage composed of black polymer sheets and glass slides to host the reactive substrate detection unit, a light emitting diode (LED) as light source, a commercially available light dependent resistor (LDR) as the photodetector to convert the optical signal transmitted through the reactive substrate detection unit in the sample stage into an electrical one, and a signal processing unit to convert the analogue electrical signal into a digital display signal.

The signal processing system is developed employing the open source Arduino UNO R3 development board, which comprises ATmega328P microcontroller apart from the Arduino integrated development environment (IDE) software for writing, compiling and uploading the programs to the microcontroller. The sample stage in the transmittance setup is assembled in such a manner that the when LED illuminates the reactive substrate detection unit the transmitted rays falls on the LDR to convert the optical signal into an analogue electrical signal.

The reactive substrate detection unit may be paper based which has distinct advantages such as biocompatibility, biodegradability, cost effectiveness, and easy disposability. Further, white background color of a filter paper makes it an excellent candidate for hosting the colorimetric assays. The system/kit can be employed for paper based point-of-care detection of a host of important biomarkers such as amylase, creatinine, and albumin from biological samples (blood, saliva) after simple modifications of the building blocks. Advantageously the said system/kit takes significantly less time to estimate the level of biomarker (such as α-amylase) in human body fluids such as blood serum, as compared to the products that are commercially available. For example, the amylase levels of different serum samples can be measured employing a standard protocol with the instrument, Dimension RxL Max Integrated Chemistry System, SIEMENS, which require time of the order of 2-3 days to determine the amylase level in blood. In comparison, with the presently reported technique, it takes a few hours to estimate the amylase level.

The microcontroller setup in the said system/kit integrates the reactive (paper) substrate, substrate holder, optical transmittance unit, and the signal processing system. The signal processing unit is adapted to be programmed in such a manner that it is capable of automatically converting the analogue electrical signal into the digital concentration signal of amylase level to give the digital display of the same.

Further, with the help of printed circuit board (PCB) prototyping the entire setup can be miniaturized into a chip.

The said system/kit has the sensitivity to measure the amylase level in the blood serum, which is in the range of, 25-100 U/L (units/litre). However, the blood serum needs a pre-treatment with potassium iodate in order to neutralize the trace of ascorbic acid present before adding on the reactive substrate detection units. Since the aforementioned range of amylase in the human blood serum is significantly small there is hardly any commercially available system/kit, which can directly measure amylase level in blood with aforementioned rapidity.

Example 1: Transmittance Based POCT System for Quantification of Biomarkers

Figure 2A:
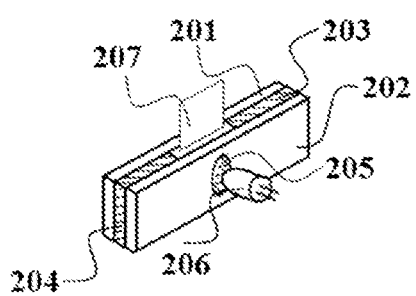
FIGS. 2A to 2E represent different parts of the sample stage, transmittance set up, and their assembly.
Figure 2B:
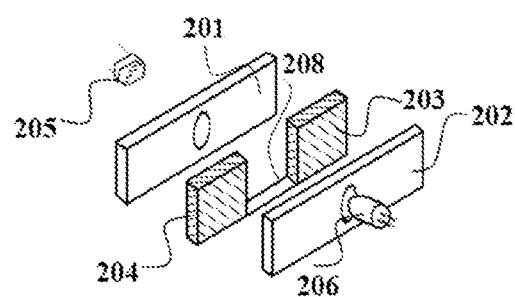
Figure 2C:
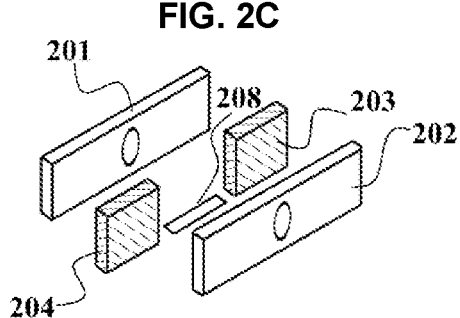

The system for point-of-care quantification of biomarkers comprises the following parts:
(a) a detection unit composed of a piece of filter paper pre-coated with reagent wherein the said reagent is expected to undergo a specific reaction with the said biomarker to generate a quantifiable optical signal, which is in proportion to the concentration of the said biomarker sample;
(b) as schematically illustrated in FIG. 1A the optoelectrochemical device composed of a sample stage (102), an optical transmittance setup (101), and a signal processing system (103), which is capable of measuring the quantifiable optical signal originating from the paper surface and perform digital display of the same,
  (i) wherein FIGS. 1B to 1F show the isometric, right, front, left, and top views with the dimensions of the said device, respectively;
  (ii) wherein the sample stage (102) is prepared to place the paper detection unit to be tested;
  (iii) wherein the transmittance setup (as illustrated in FIGS. 2A and 2B) comprises an LED light source and a photodetector (LDR), which confines the sample stage from two sides, wherein the light source illuminates the reagent coated paper detection unit and the transmitted light through the paper is collected on a photodetector;
  (iv) wherein the quantifiable optical signal transmitted through the reagent coated paper detection unit is transduced to electrical signal by the photodetector; and
  (v) wherein the analogue electrical signal produced in the transmittance setup is transduced into a digital display signal using a signal processing system. The signal processing unit is adapted to be advantageously further calibrated to measure the specific biomarker level in the biological sample.

FIGS. 2A and 2B illustrate the different components of the transmittance setup (101) where (201) and (202) are black polymer sheets with circular holes bored in them to house the LDR photodetector (205) and the light source LED (206). The glass slide fragments (203) and (204) are sandwiched between the polymer sheets 201 and 202 to form the sample stage for the paper detection unit (207). Polymer sheet 208 forms the bottom of the blank space in the sample stage as shown in FIG. 2B.

Figure 2D:
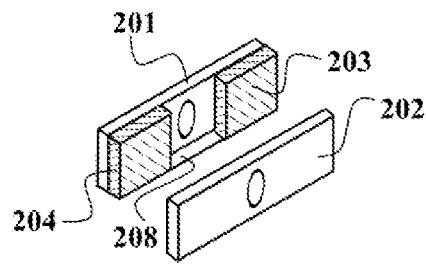
Figure 2E:
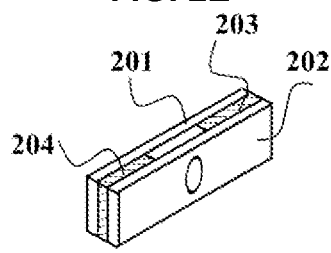

FIGS. 2B to 2E illustrate the assemblage of the sample stage (102). Glass slide fragments 203 and 204 are first attached to polymer sheet 201 using adhesive in a manner that the space between 203 and 204 is approximately equal to the size of the paper detection units. Polymer sheet 202 is then attached to glass slide fragments 203 and 204 with adhesive, thus creating the sample stage for the paper detection units, (FIGS. 2D to 2E). Importantly to favor integration of the detection system/kit for ready analysis, the substrate chamber was maintained dark such as by covering with black polymer sheets to create dark conditions around the paper substrate.

The signal processing unit of the said device is developed employing the open source Arduino UNO R3 Development board which consists of ATmega 328P microcontroller apart from the Arduino integrated development environment (IDE) software for writing, compiling and uploading the programs to the microcontroller wherein the interfacing of the optical transmittance setup with the Arduino Uno R3 development board is done to transduce the analogue electrical signal generated by the transmittance setup into a digital signal.

The ATmega328P microcontroller consisted of 14 digital input/output pins. There were 6 pins for analogue inputs, which could be used to interface sensors and actuators. The clock pulse to the microcontroller was given by 16 MHZ ceramic resonator. The onboard USB port could be used for both programming and supplying power to the microcontroller also a separate power jack was included for supplying power to the microcontroller board. The microcontroller had an integrated 10 bit ADC (analogue to digital convertor) for digitizing the analogue inputs. The analogue input from transmittance set up was given to the analogue input A0 port on the Arduino UNO R3 development board.

Figure 3:
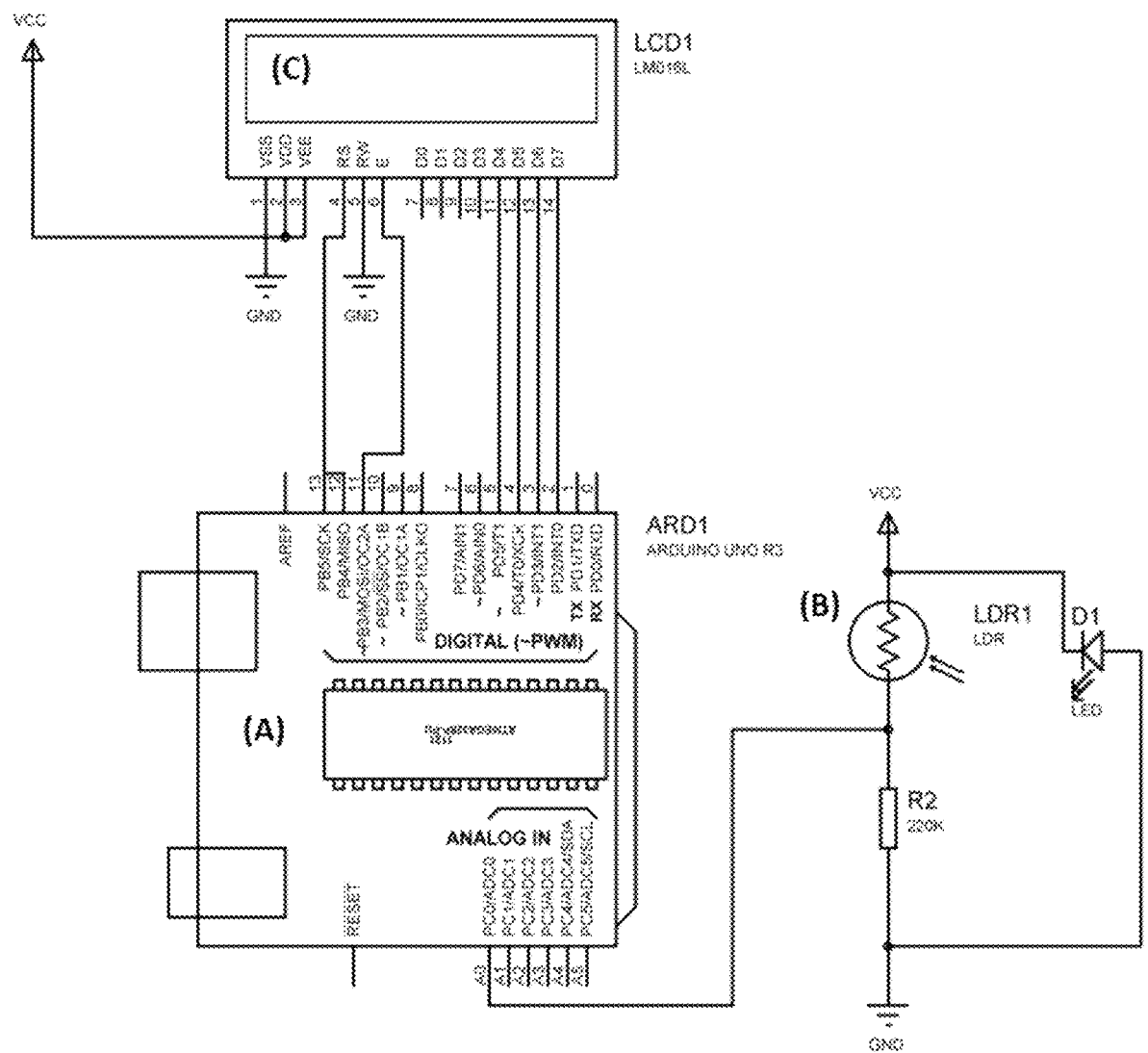
FIG. 3 illustrates the circuit diagram for the optoelectronic signal processing system.

FIG. 3 illustrates the circuit diagram of the said device where part (A) represents the open source Arduino Uno R3 development board. The VCC and the GND in the circuit diagram represents the supply voltage and ground, respectively. The analogue input from transmittance set up B (101) is supplied to the analogue input A0 port on the Arduino UNO R3 development board. The resistor R2 (220 KΩ) is connected to the ground. The LED D1 (206) is connected to the supply voltage. Part (C) represents the LCD. The pins 2 and 3 of LCD are connected to the supply voltage while pin 1 is connected to the ground. The controlling pins of LCD 4 and 6 are connected to the pins 12 and 11 of the development board (A) while pin 5 of LCD is connected to the ground. The data pins 11, 12, 13, and 14 of LCD are connected to the pins 5, 4, 3, and 2 of the development board, respectively.

Figure 4A:
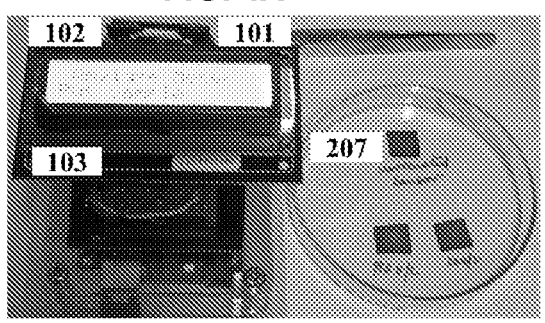
FIGS. 4A and 4B represent the photographs of the proposed prototype.
Figure 4B:
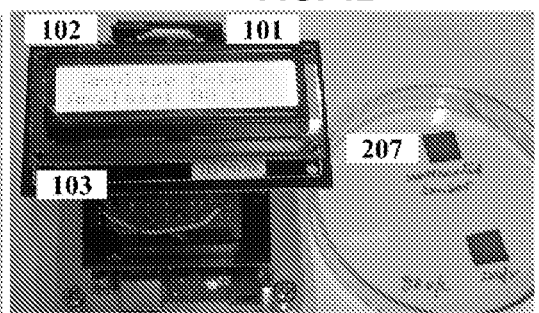
Figure 4C:
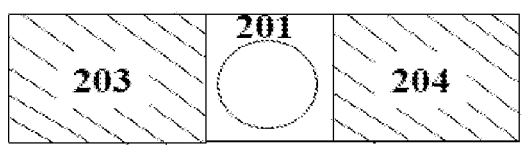
FIGS. 4C to 4E represent the line drawing of the assembled sample stage.
Figure 4D:
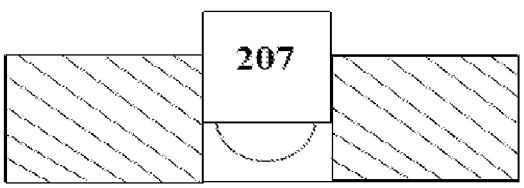
Figure 4E:
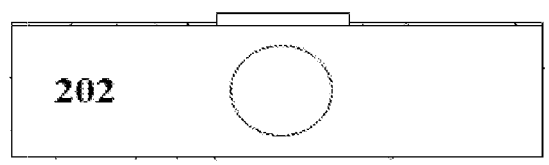

FIGS. 4A to 4E show the photographs of the optoelectrochemical device composed of a sample stage (102), an optical transmittance setup (101), and a signal processing system (103), which is capable of measuring the quantifiable optical signal originating from the paper surface and perform digital display of the same. FIGS. 4A and 4B show the outputs in presence and in absence of the substrate. FIGS. 4C to 4E show the assemblage of the sample stage (102). Glass slide fragments 203 and 204 are first attached to polymer sheet 201 using adhesive in a manner that the space between 203 and 204 is approximately equal to the size of the paper detection units. Polymer sheet 202 is then attached to glass slide fragments 203 and 204 with adhesive, thus creating the sample stage for the paper detection units.

Example 2: Measurement of Concentration of Biomarker α-Amylase

Quantitative estimation of α-amylase was done using the system as described in Example 1 following the steps as described hereunder:
 i. Preparation of Reagents:
  a) The starch solution was prepared by dissolving starch in distilled water and then heating until the solution became transparent. The iodine solution was prepared by dissolving suitable amounts of potassium iodide and iodine in distilled water. The starch and iodine solutions were prepared by mixing equal volumes of starch and iodine solutions of suitable concentrations resulting in the Prussian blue color of the mixture.
  b) A stock α-amylase solution was prepared by dissolving procaine α-amylase in phosphate buffer solution of pH 7. The stock was then diluted to different concentrations
 ii. Preparation of Reactive Substrate Detection Units:
 The reactive substrate detection unit was prepared by cutting filter paper into small pieces of appropriate shapes and sizes followed by coating of the starch-iodine reagent and subsequent drying to ensure uniform Prussian blue coloration on the surface.
 iii. Chemical Reaction:
 The method is based on a standard reaction between Prussian blue colored starch-iodine solution and α-amylase, wherein α-amylase cleaves the α-1,4 glycosidic linkages in starch to form simple sugars which do not react with iodine solution resulting in fading of the color.
 iv. Mechanism:
  (a) When aqueous α-amylase solution was added on these Prussian blue colored paper detection unit, the blue coloration faded away because of the very specific reaction of α-amylase with starch when it hydrolyzed starch into simpler carbohydrates subsequently releasing iodine. The variations in the blue color on the paper surface were found to have a linear correlation with the α-amylase concentration in the aqueous solution, wherein the reduction in the intensity of the blue coloration on the paper detection units was observed with increase in the amylase in the aqueous solution.
  (b) The variation in the colorimetric signal was quantified by the aforementioned optoelectrochemical device of the Example 1. The paper detection units were placed easily into the sample stage (102) in the device of Example 1. The transmittance setup confined the sample stage between the LED light source (206) to illuminate the paper surface from one side and an LDR photodetector (205) on the opposite side of the light source to capture the transmitted rays coming out of the paper detection unit. The arrangement in the transmittance setup ensured that the optical signal was converted into an electrical one.
  (c) Accordingly, the intensity of the transmitted light coming out of the paper detection unit varied with the fading of the blue coloration on the paper surface with increase in the amylase activity; wherein the variations in the intensity of the transmitted light with the variation in amylase activity generated different electrical resistances on the LDR.
 v. Preparation of Calibration Curve:
 To correlate the concentration of α-amylase to the color change of the detection strips, a calibration curve was prepared (FIG. 5) by plotting the normalized change in resistance of the photoresistor against the concentration of α-amylase.

FIG. 5 represents the experimental calibration curve showing the variation of the normalized resistance difference ($\Delta R_N^T$) with concentration of α-amylase (C). The normalized resistance difference ($\Delta R_N^T$) is defined as $\Delta R_N^T = (R_i^T - R_f^T)/R_i^T$, where $R_i^T$ is electrical resistance measured for the detection strip before the addition of the amylase and $R_f^T$ is the resistance shown by the photoresistor after the addition of amylase to the paper detection unit.

To prepare the calibration curve, initially, the resistance showed by the photoresistor for a number of starch iodine embedded paper detection units was noted. Then α-amylase solutions of different concentrations were added to the paper detection units and they were incubated for a suitable time period. Resistance measurements were again carried out for the α-amylase loaded paper detection units. It was found that the resistance showed by the photoresistor for the virgin paper detection units was more than the resistance shown after α-amylase addition to the strips. The difference in resistance was found to vary almost linearly with α-amylase concentration, as shown in FIG. 5.

With an increase in amylase concentration, the increased hydrolysis of starch led to the weakening of the blue coloration of the paper detection units. Moreover, due to breakdown of the starch-iodine complex, a portion of the embedded iodine evaporated from the paper surface leading to the opening of the pores for light transmittance through the paper detection units. Thus, the fading of the paper detection units led to the larger optical transmittance which in turn led to the reduction in the resistance of the photoresistor. Thus, the difference in the base resistance of a virgin paper detection unit with the one where amylase was added increased with the increase in the amylase concentration in the sample, as shown in FIG. 5.

Further, the analogue electrical signal thus generated in the transmittance set up was converted into suitable digital signal for displaying the amylase concentration using a signal processing system as described in Example 1. The signal processing unit was programmed with the aforementioned calibration of variation of known amylase concentration with the variation in the Prussian blue coloration stabilized on the paper detection unit; wherein the amylase concentration in the unknown sample was displayed in an LCD with the help of the known calibration program.

It is thus possible by way of the present invention to provide an integrated transmittance based optoelectrochemical system for point-of-care detection and quantification of clinically important biomarkers from the biological samples. The system/kit of the present advancement would enable for the first time to measure and quantify the variations in the optical signals originating from the chemical reactions on reactive substrate detection units and convert the optical signals to electrical and finally to a digital display in a single step process. The said integrated system would enable for the first time rapid and efficient quantification of the biomarkers avoiding existing multistep tedious processes. The system is easily portable, energy efficient, and ecofriendly does not require trained personnel and advanced infrastructure and may also find applications in testing water, food, soil, air quality, and for pH measurements, where there is a colorimetric change on a paper surface with the change in pH of a solution.

We claim:

1. An optical signal transmittance based system for point-of-care quantification of biomarker samples comprising:
   a sample stage;
   a detection unit;
   an optical transmission unit; and
   signal processing unit characterized in that
   the sample stage for supporting the detection unit including a light transmittable reactive substrate including paper based reactive substrates confined by a compact optical transmission unit comprising of an illumination source and a photodetector such that light from the light source falls on the photodetector after transmitted through the light transmittable reactive substrate capable of undergoing a specific biomarker sample interactive reaction based change in color intensities and generate a quantifiable optical signal based on the change in color intensities proportional to the concentration of the biomarker sample;
   the photodetector transducing the quantifiable optical signal transmitted through the light transmittable reactive substrate to electrical signal;
   the signal processing unit operatively connected to the photodetector for measurable variable resistance proportionate to the specific biomarker sample interactive reaction-based change in color intensities for ready and fast direct point of care quantification of biomarker samples.

2. An optical signal transmittance based system as claimed in claim 1, wherein the signal processing unit comprises a display for ready displaying of the quantified level of the biomarker.

3. An optical signal transmittance based system as claimed in claim 1, wherein the light transmittable reactive substrate is selected from paper coated with starch-iodine for amylase detection, paper coated with picric acid and sodium hydroxide for creatinine detection, and paper coated with bromophenol blue for albumin detection.

4. An optical signal transmittance based system as claimed in claim 1,
   comprising the photo-detector transducing the quantifiable optical signal transmitted through the light transmittable reagent coated paper substrate to electrical signal; and
   the signal processing unit transducing analogue electrical signal produced in the transmittance unit into a digital display signal.

5. An optical signal transmittance based system as claimed in claim 1, wherein the analogue electrical signal obtained from LDR is automatically converted into a digital signal through the signal processing unit for digital display, the signal processing unit calibrated to measure the biomarker level.

6. An optical signal transmittance based system as claimed in claim 1, wherein the light transmittable reactive substrate comprises a filter paper cut into pieces of appropriate size and shape fitting into the dark chamber of the sample stage and pre-coated with the reagent and dried.

7. An optical signal transmittance based system as claimed in claim 1, wherein the light transmittable reactive substrate having pretreated reagent is colored, which upon reaction with the biomarker sample generates the quantifiable optical signal proportional to the concentration of the biomarker sample.

8. A method for point-of-care quantification of biomarkers sample involving the optical signal transmittance based system as claimed in claim 1, comprising:
   (a) providing on the sample stage the light transmittable reactive substrate pretreated with the reagent to undergo a specific biomarker sample interactive reaction;
   (b) reacting the thus pre-treated the light transmittable reactive substrate with a biomarker sample for developing a substrate-biomarker sample by illuminating the thus reacted pre-treated light transmittable reactive substrate including paper based reactive substrates with the biomarker sample with the LED on one side of the light transmittable reactive substrate and involving a the photodetector on the other side of the light transmittable reactive substrate;
   characterized in that the light transmittable reactive substrate pre-treated with a reagent capable of undergoing a specific biomarker sample interactive reaction include colored reagent which upon interaction with the biomarker sample generates the quantifiable change in color based
   quantifiable optical signal proportional to the concentration of the biomarker sample involving
   (c) carrying out signal processing for quantification of the biomarker sample based on the optical signal generated from the substrate-biomarker sample reaction based on quantification of the optical signal to electrical signal involving the signal processing unit operatively connected to the photodetector for measurable variable resistance proportionate to the specific biomarker sample interactive reaction for ready and fast direct point of care quantification of biomarker samples.

9. A method as claimed in claim 8, comprising selectively providing the color of the paper substrate having pretreated reagent such that, which upon interaction with biomarker sample leads to a very specific reaction leading to the fading of the color of the reagent coated paper; wherein the intensity of the color varies with the concentration of the analyte in the bio-sample.

10. A method as claimed in claim 8, comprising
(a) providing color of the reagent coated paper substrate as Prussian blue colored starch-iodine coated paper which upon interaction with aqueous α-amylase solution on the blue colored starch-iodine coated paper detection units leads to a very specific reaction leading to the fading of the Prussian blue color of the paper;
(b) wherein the intensity of the Prussian blue color varies with the concentration of the α-amylase in the bio-sample; and
(c) wherein the reduction in the intensity of the blue coloration on the paper detection units can be observed with increase in the amylase in the aqueous solution.

11. A method as claimed in claim 8,
(a) wherein the intensity of the transmitted light passing though the light transmittable reactive paper substrate in the detection unit varied with the fading of the blue coloration on the paper surface with increase in the amylase activity;
(b) wherein the variations in the intensity of the transmitted light with the variation in amylase activity generated different analogue electrical signals on the photodetector including LDR;
(c) wherein the light transmittance based optical signal originating from the chemical response of the reagent coated light transmittable reactive paper substrate is converted into an analogue electrical signal by the calibrated signal processing unit; and
(d) displayed in the display means or report generated based thereon with the help of the calibrated signal processing unit.

12. An optical signal transmittance based system as claimed in claim 1 comprising:
the sample stage supporting the light transmittable reactive substrate comprise a dark/black substrate chamber covered with black polymer sheets attached to glass slides providing for the dark/black substrate chamber with dark conditions around the light transmittable reactive substrate in the dark/black substrate chamber, the black polymer sheets having opening bored in them to house the LDR photodetector and the light source LED respectively, in such a manner that illumination from the LED falls directly on the light transmittable reactive substrate inside the dark/black substrate chamber through one of the opening on the before generating the optical signal from the reactive substrate into the LDR through the other opening of the dark/black substrate chamber, minimizing the loss of optical signal and providing the compact optical transmission unit with respect to the dark/black substrate chamber supporting the light transmittable reactive substrate;
the signal processing unit operatively connected to the light dependent resistor (LDR) photodetector and including a microprocessor to facilitate a single step signal processing without loss of the optical signal.

13. An optical signal transmittance based system/kit as claimed in claim 1 wherein the light transmittable reactive substrate comprises pre reagent-treated substrate based on the selective bio marker sample to be quantified and can include combinations selected from:
for a-amylase enzyme biomarker sample providing starch-iodine reagent treated paper substrate;
for creatinine biomarker sample providing picric acid and sodium hydroxide reagent treated paper substrate
for albumin biomarker sample providing bromophenol blue reagent treated paper substrate.

\* \* \* \* \*